United States Patent [19]
Motley et al.

[11] Patent Number: 5,783,200
[45] Date of Patent: Jul. 21, 1998

[54] PERSONAL CLEANSING COMPOSITIONS

[75] Inventors: Curtis Bobby Motley, West Chester; Robert Lee Wells, Cincinnati, both of Ohio

[73] Assignee: The Procter & Gamble Company, Cincinnati, Ohio

[21] Appl. No.: 786,521

[22] Filed: Jan. 21, 1997

[51] Int. Cl.$^6$ ............................................. A61K 6/00
[52] U.S. Cl. ..................... 424/401; 510/156; 510/159; 510/426; 510/428; 510/472
[58] Field of Search ....................... 424/401; 510/156, 510/472, 159, 426, 428

[56] References Cited

U.S. PATENT DOCUMENTS

| | | | |
|---|---|---|---|
| 2,979,465 | 4/1961 | Parran et al. | |
| 3,179,599 | 4/1965 | Eaton et al. | |
| 4,491,539 | 1/1985 | Hoskins et al. | 510/472 |
| 4,556,510 | 12/1985 | Holsopple | 252/547 |
| 4,557,928 | 12/1985 | Glover | |
| 4,617,148 | 10/1986 | Shields | 252/547 |
| 4,678,606 | 7/1987 | Akhter et al. | 252/542 |
| 4,683,004 | 7/1987 | Goddard | 106/170 |
| 4,702,905 | 10/1987 | Mitchell et al. | 424/57 |
| 4,725,433 | 2/1988 | Matravers | 424/70 |
| 4,917,823 | 4/1990 | Maile, Jr. | 252/548 |
| 5,019,376 | 5/1991 | Uick | 424/70 |
| 5,057,241 | 10/1991 | Merritt et al. | 252/174.17 |
| 5,059,414 | 10/1991 | Dallal et al. | 424/70 |
| 5,084,212 | 1/1992 | Farris et al. | |
| 5,137,718 | 8/1992 | Gillespie | 424/78.24 |
| 5,141,664 | 8/1992 | Corring et al. | 252/90 |
| 5,154,847 | 10/1992 | LaPetina et al. | 424/705 |
| 5,160,448 | 11/1992 | Corring | 252/95 |
| 5,292,528 | 3/1994 | Mori et al. | 424/54 |
| 5,340,571 | 8/1994 | Grace | 424/73 |
| 5,443,814 | 8/1995 | Illig et al. | 424/9.45 |
| 5,514,369 | 5/1996 | Salka et al. | 424/70.1 |

FOREIGN PATENT DOCUMENTS

| | | | |
|---|---|---|---|
| 170927 | 11/1985 | European Pat. Off. | A61K 7/08 |
| 191564 | 8/1986 | European Pat. Off. | A61K 7/075 |
| 317314 | 5/1989 | European Pat. Off. | A61K 7/06 |
| 400914 | 6/1989 | European Pat. Off. | A01N 25/16 |
| 413317 | 6/1990 | European Pat. Off. | A61K 7/08 |
| 413416 | 2/1991 | European Pat. Off. | A61K 7/06 |
| 562638 | 3/1993 | European Pat. Off. | A61K 7/08 |
| 4413430 | 4/1994 | European Pat. Off. | A61K 7/075 |
| 63-161083 | 12/1986 | Japan | C11D 3/382 |
| 62-263297 | 11/1987 | Japan | C11D 3/37 |
| 2164255 | 3/1986 | United Kingdom | A61K 7/16 |
| WO 91/07943 | 6/1991 | WIPO | A61K 7/15 |
| WO 91/17237 | 11/1991 | WIPO | C11D 17/00 |
| WO 92/05234 | 4/1992 | WIPO | C11D 1/32 |
| WO 94/16680 | 8/1994 | WIPO | A61K 7/50 |
| Wo 96/17916 | 6/1996 | WIPO | C11D 1/38 |
| Wo 96/17917 | 6/1996 | WIPO | C11D 1/66 |
| Wo 96/29979 | 10/1996 | WIPO | A61K 7/50 |

OTHER PUBLICATIONS

Abstract 79-37651B (Japan) A61K 007–06 No translation.
Abstract 79-37650B (Japan) A61K 007–06 No translation.
Abstract 83-841087 (Japan) A61K 007–06 No translation.
Abstract 87-350995 (Japan) A61K 007–06 No translation.

*Primary Examiner*—Joseph L. Schofer
*Assistant Examiner*—N. Sarofim
*Attorney, Agent, or Firm*—Darryl C. Little; Tara M. Rosnell

[57] ABSTRACT

The compositions of the present invention relate to improved personal cleansing compositions comprising a surfactant system comprising at least one surfactant selected from the group consisting alkyl glyceryl ether sulphonate surfactants, from above about 0.1% of a nonionic or anionic water soluble polymer, a phase separation initiator and water. These compositions provide improved lathering and conditioning benefits.

20 Claims, No Drawings

PERSONAL CLEANSING COMPOSITIONS

FIELD OF THE INVENTION

The present invention relates personal cleansing compositions comprising a cleansing component together with a conditioning component.

BACKGROUND OF THE INVENTION

Human hair becomes soiled due to its contact with the surrounding atmosphere and, to a greater extent, from sebum secreted by the head. The build-up of the sebum causes the hair to have a dirty feel and an unattractive appearance. The soiling of the hair necessitates it being shampooed with frequent regularity.

Shampooing the hair cleans by removing excess soil and sebum. However, the shampooing process has disadvantages in that the hair is left in a wet, tangled and generally unmanageable state. Shampooing can also result in the hair becoming dry or "frizzy", and a loss of luster, due to removal of natural oils or other hair moisturizing materials. After shampooing, the hair can also suffer from a loss of "softness" perceived by the user upon drying. The hair can also suffer from increased levels of static upon drying after shampooing. This can interfere with combing and can result in fly-away hair. A variety of approaches have been developed to alleviate the after-shampoo problems. These range from the inclusion of hair conditioning aids in shampoos to post-shampoo application of hair conditioners, i.e., hair rinses. Hair rinses are generally liquid in nature and must be applied in a separate step following the shampooing, left on the hair for a length of time, and rinsed with fresh water. This, of course, is time consuming and is not as convenient as shampoos containing both cleaning and hair conditioning ingredients.

While a wide variety of shampoos have been disclosed which contain conditioning aids, they have not been totally satisfactory for a variety of reasons. Cationic conditioning agents are highly desirable for use in hair conditioning due to their abilities to control static, improve wet detangling, and provide a silky wet hair feel to the user. One problem which has been encountered in shampoos relates to compatibility problems between good cleaning anionic surfactants and the many conventional cationic agents which historically have been used as conditioning agents. Efforts have been made to minimize adverse interaction through the use of alternate surfactants and improved cationic conditioning agents. Cationic surfactants which provide good overall conditioning in hair rinse products, in general, tend to complex with anionic cleaning surfactants and provide poor conditioning in a shampoo context. In particular, the use of soluble cationic surfactants that form soluble ionic complexes do not deposit well on the hair. Soluble cationic surfactants that form insoluble ionic complexes deposit on the hair but do not provide good hair conditioning benefits, and tend to cause the hair to have a dirty, coated feel. The use of insoluble cationic surfactants, e.g., tricetyl methyl ammonium chloride, can provide excellent anti-static benefits but do not otherwise provide good overall conditioning. Many cationic polymers tend to build up on the hair, resulting in an undesirable, "unclean" coated feel. Cationic polymers therefore, conventionally, are preferably used at limited levels to minimize this problem. This, however, can limit the overall conditioning benefits that are obtained. Additionally, cationic conditioning agents commonly do not provide optimal overall conditioning benefits, particularly in the area of "softness", especially when delivered as an ingredient in a shampoo composition.

Materials which can provide increased softness are nonionic silicones. Silicones in shampoo compositions have been disclosed in a number of different publications. Such publications include U.S. Pat. No. 2,826,551, Geen, issued Mar. 11, 1958; U.S. Pat. No. 3,964,500, Drakoff, issued Jun. 22, 1976; U.S. Pat. No. 4,364,837, Pader, issued Dec. 21, 1982; and British Patent 849,433, Woolston, issued Sep. 28, 1960. While these patents disclose silicone containing compositions, they also did not provide a totally satisfactory product in that it was difficult to maintain the silicone well dispersed and suspended in the product. Recently, stable, insoluble silicone-containing hair conditioning shampoo compositions have been described in U.S. Pat. No. 4,741,855, Grote and Russell, issued May 3, 1988 and U.S. Pat. No. 4,788,066, Bolich and Williams, issued Nov. 29, 1988. These shampoo compositions can deliver excellent overall conditioning benefits to the hair while maintaining excellent cleaning performance, even with the use of anionic detersive surfactants, for a wide variety of hair types.

More recently, improved conditioning shampoos were provided in U.S. Ser. No. 07/622,699, Robert L. Wells, filed Dec. 5, 1990, now abandoned, and its continuation application Ser. No. 07/778,765, filed Oct. 21, 1991, wherein shampoos containing anionic surfactant, dispersed, insoluble silicone, and certain relatively low ionic strength cationic polymers (greater than about 0.4 meq./gm) were disclosed. These compositions provide excellent hair cleaning and conditioning to a wide variety of hair types, especially including improved conditioning to hair damaged by color treatments, bleaching, permanents, etc.

Japanese Patent Application, Laid Open No. 56-72095, Jun. 16, 1981, Hirota et al. (Kao Soap Corp.) also discloses shampoo containing cationic polymer and silicone conditioning agents. Still other patent publications relating to shampoos with cationic agents and silicone include EPO Application Publication 0 413 417, published Feb. 20, 1991, Hartnett et al.

Another approach to providing hair conditioning benefits to shampoo compositions has been to use materials which are oily to the touch. These materials provide improved luster and shine to the hair. Oily materials have also been combined with cationic materials in the shampoo formulations. Japanese Patent Application Showa 53-35902, laid open Oct. 6, 1979 (Showa 54-129135), N. Uchino (Lion Yushi Co.), discloses hair treatment compositions containing cationic polymer, fatty acid salt, and at least 10% of an oily component for use before or after shampooing. Suitable oily components are hydrocarbons, higher alcohols, fatty acid esters, glycerides, and fatty acids. Japanese Patent Application 62 [1987]-327266, filed Dec. 25, 1987, published Jul. 4, 1989, laid open No. HEI 1[1987]-168612, Horie et al., discloses detergent compositions containing cationic surfactant and/or cationic polymer, anionic surfactant, and specific esters of the formula RCOOR' wherein R and R' are straight or branched chain alkyls.

In spite of these attempts to provide optimal combinations of cleaning ability and hair conditioning, there remains a need for personal cleansing compositions providing improved lathering and conditioning benefits. The present inventor has found that compositions combining certain nonionic or anionic polymers, a minimum level of a phase separation initiator and a surfactant system comprising an alkyl glyceryl sulfonate surfactant form stable aqueous emulsions - wherein the emulsion comprises aqueous polymer phase droplets suspended in an aqueous surfactant phase. The dispersed, concentrated polymer phase provides improved hair and skin conditioning without sacrificing clean feel. These compositions can be made into any of a number of conventional forms including, but not limited to, conditioning shampoos, foams, mousses, gels, lotions, sprays and the like.

In addition to the afore-mentioned hair care benefits, it has been found that the nonionic or anionic polymer and surfactant system emulsion of the present invention is also useful for incorporation into a wide variety of personal skin cleansing compositions or used in conjunction with lathering instruments. These compositions provide a skin conditioning component which is more easily and uniformly deposited upon the skin and feel good upon the skin. Such compositions include liquid soaps, shower gels, lotions and the like. Suitable lathering instruments include nonwoven substrates, woven substrates, hydroentangled substrates, air entangled substrates, natural sponges, synthetic sponges, polymeric netted meshes, and the like.

Accordingly, it is an object of this invention to provide personal cleansing compositions providing improved lathering and conditioning.

Another object of the present invention is to provide improved personal cleansing compositions comprising a nonionic or anionic polymer, a surfactant system, a minimum amount of a phase separation initiator and an alkyl glyceryl sulfonate.

One other object of the present invention is to provide personal cleaning compositions which exist as an emulsion comprising a polymer concentrated aqueous phase in an aqueous surfactant phase.

Still another object of the present invention is to provide personal cleansing compositions which can comprise lower levels of surfactant.

Another object of the present invention is to provide all in one shampoo plus conditioner compositions which can provide excellent cleaning performance and improved levels of conditioning while minimizing any adverse side effects associated with build-up due to the use of excess conditioning agent.

It is also an object of this invention to provide a method for cleaning and conditioning the hair and skin which can provide excellent cleaning in combination with improved conditioning.

These and other objects will become readily apparent from the detailed description which follows.

SUMMARY OF THE INVENTION

The compositions of the present invention relate to personal cleansing composition in the form of a stable aqueous emulsion, comprising:

a.) from about 4% to about 50%, by weight, of a surfactant system wherein said surfactant system comprises from about 0.5% to about 20%, by weight, of at least one surfactant selected from the group consisting of alkyl glyceryl sulfonates, derivatives thereof and salts thereof;

b.) at least above about 0.1%, by weight, of a nonionic or anionic, water soluble polymer;

c.) from about 0.1% to about 5%, by weight, of a phase separation initiator selected from the group consisting of electrolytes, amphiphiles and mixtures thereof; and d.) from about 50% to about 95%, by weight, of water.

The compositions of the present invention preferably form visually distinct droplets.

The present invention further relate to methods of using the personal cleansing compositions.

DETAILED DESCRIPTION OF THE INVENTION

The personal cleansing compositions of the present invention can comprise, consist of, or consist essentially of the essential elements and limitations of the invention described herein, as well any of the additional or optional ingredients, components, or limitations described herein.

All percentages, parts and ratios are based upon the total weight of the personal cleansing compositions of the present invention, unless otherwise specified. All such weights as they pertain to listed ingredients are based on the active level and, therefore, do not include carriers or by-products that may be included in commercially available materials, unless otherwise specified.

The term "phase separation", as used herein means the formation of two thermodynamically stable liquid phases which exist, not as distinct bulk layers, but as a stable emulsion comprising droplets of one phase dispersed in another phase.

The term "visually distinct", as used herein, refers to droplets or droplet phases suspended in a continuous phase such that, optically, the droplets or droplet phases are visually separate and distinct from the continuous phase when viewed by the unaided eye.

As used herein, the term "water soluble" refers to any material that is sufficiently soluble in water to form a substantially clear solution to the naked eye at a concentrations of 1.0% or more by weight of the material in the water at 25° C. Conversely, the term "water insoluble" refers to all materials that are not sufficiently soluble in water to form a substantially clear solution to the naked eye at a concentration of about 1.0% or more by weight of the insoluble material in water at 25° C.

The personal cleansing compositions of the present invention, including the essential and optional components thereof, are described in detail hereinafter.

Essential Components

Surfactant System

The compositions of the present invention comprise as an essential component a suitable surfactant system. The surfactant system of the present invention comprises a variety of detersive surfactants. The purpose of the detersive surfactant is to provide cleaning performance to the composition.

The surfactant system of the present invention is preferably present in the personal cleansing compositions at a level of from about 4% to about 50%, more preferably from about 4% to about 40%, still more preferably from about 4% to about 30%, even more preferably from about 5% to about 20% and most preferably from about 6% to about 16%. It should be recognized , however, that the concentration of the surfactant system may vary with the cleaning or lather performance desired, the surfactants incorporated into the surfactant system, the desired product concentration, the presence of other components in the composition, and other factors well known in the art.

An essential component of the surfactant system of the present invention is a surfactant selected from the group consisting of alkyl glyceryl ether sulfonate surfactants (also referred to herein as an "AGS" surfactant), derivatives thereof and salts thereof. These compositions comprise from about 0.5% to about 20%, more preferably from about 1% to about 10%, and most preferably from about 2% to about 8% of the alkyl glyceryl ether sulfonate surfactant. These AGS surfactants are derived from an alkyl glyceryl ether containing a sulfonate or sulfonate salt group. These compounds generally can be described as an alkyl monoether of glycerol that also contains a sulfonate group.

These AGS surfactants can be described as generally conforming to the following structures:

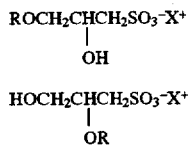

wherein R is a saturated or unsaturated straight chain, branched chain, or cyclic alkyl group having from about 10 to about 18 carbon atoms, preferably from about 11 to about 16 carbon atoms, and most preferably from about 12 to about 14 carbon atoms, and X is a cation selected from the group consisting of ammonium; mono-alkylsubstituted ammonium; di-alkylsubstituted ammonium; tri-alkylsubstituted ammonium; tetra-alkylsubstituted ammonium; alkali metal; alkaline metal; and mixtures thereof. More preferably, the alkyl radicals, R in the above formulas, are saturated and straight chain.

Without being limited by theory, it is believe that the distribution of alkyl chain lengths in the AGS surfactant has some effect on the character of the overall cleansing composition. A satisfactory distribution can be achieved in a commercially practicable way by using fatty alcohols derived from coconut oil and tallow. An equivalent distribution of alkyl chain lengths can be achieved using other starting materials. In the preparation of the coconut fatty alcohols used to provide the alkyl group of the AGS, preferably the middle cut of the coconut oil is taken. The higher boiling cut can be retained with the middle cut coconut oils if desired. In the preparation of the tallow fatty alcohols, a hydrogenation step is included to insure that they are substantially saturated.

The preferred AGS compounds are those where the alkyl group is derived from at least about 50% from alcohols of about 10 to about 18 carbons, having mainly monoglyceryl radicals present, with less than about 30% of diglyceryl radicals present. The AGS used in the Examples described below contains about 15% of diglyceryl ether sulfonates, and is preferred because of the ease of manufacturing this material. The term "AGS" is intended to include monoglyceryl, diglyceryl, and traces of the higher glyceryl compounds. Small amounts, that is less than about 3% total, of triglyceryl ether sulfonates and tetraglyceryl ether sulfonates can be present. Also included are AGS's derived from glyceryl ethers having branched or mixed branched and straight chain lengths that emulate the straight chain lengths.

The more preferred AGS surfactants for use in this invention are those which have a $C_{12-14}$ straight chain length, and are crystalline in structure. The preferred cation, "X", in the AGS surfactants is sodium. An example of a commercially available AGS surfactant useful herein includes sodium cocoglyceryl ether sulfonate, as listed in CTFA *International Cosmetic Ingredient Dictionary*, fifth edition, 1993, page 660, which is incorporated by reference herein in its entirety.

The AGS surfactants of this invention can be prepared using a variety of standard synthetic methods. The AGS surfactants can be preferably prepared by reacting fatty alcohols with a slight excess of epichlorohydrin, and then sulfonating the resulting chloroglyceryl ethers by means of the Streckerization Reaction. Secondary reaction products, such as alkyl diglyceryl ether disulfonates,

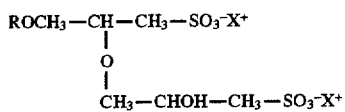

are formed in addition to the alkyl monoglyceryl ether sulfonate which is the primary product. Additional isomers of the diglyceryl compound are also formed and can be monosulfonated or disulfonated. For the purposes of this invention, the sodium alkyl glyceryl ether sulfonate should contain less than about 30% of the diglycerol ether product, and preferably less than about 25%. The balance is substantially monoglyceryl ether sulfonate. Generally, it is not desirable to reduce the alkyl diglyceryl ether content below about 5% for economic reasons.

The AGS surfactants useful in the present invention are more fully described in U.S. Pat. No. 2,979,465, to Parran et al., issued Apr. 11, 1961; U.S. Pat. No. 3,179,599, to Eaton et al., issued Apr. 20, 1965; British Patent No. 848,224, published Sep. 14, 1960; British Patent No. 791,415, published Mar. 5, 1958; U.S. Pat. No. 5,322,643, to Schwartz et al., issued Jun. 21, 1994; and U.S. Pat. No. 5,084,212, to Farris et al. issued Jan. 28, 1992; which are all hereby incorporated herein by reference in their entirety. These references also disclose various cleansing products in which the AGS surfactant of this invention can be used.

The surfactant system of the present invention also preferably includes additional surfactants selected from the group consisting of amphoteric, anionic surfactants and mixtures thereof. Amphoteric surfactant components useful in the present composition include those known to be useful in personal care cleansing compositions, and which, preferably, contain a group that is anionic at the pH of the compositions of the present invention. The concentration of such surfactant components in the surfactant system of the present invention preferably ranges from about 0.5% to about 20%, more preferably from about 1% to about 10%, and most preferably from about 2% to about 7% by weight of the surfactant system. Examples of amphoteric surfactants suitable for use in the personal cleansing composition herein are described in U.S. Pat. Nos. 5,104,646 (Bolich Jr. et al.), U.S. Pat. No. 5,106,609 (Bolich Jr. et al.), which descriptions are incorporated herein by reference. Examples of amphoteric detersive surfactants which can be used in the compositions of the present invention are those which are broadly described as derivatives of aliphatic secondary and tertiary amines in which the aliphatic radical can be straight or branched chain and wherein one of the aliphatic substituents contains from about 8 to about 18 carbon atoms and one contains an anionic water solubilizing group, e.g., carboxy, sulfonate, sulfate, phosphate, or phosphonate. Examples of compounds falling within this definition are sodium 3-dodecyl-aminopropionate, sodium 3-dodecylaminopropane sulfonate, sodium lauroamphoacetate, N-alkyltaurines such as the one prepared by reacting dodecylamine with sodium isethionate according to the teaching of U.S. Pat. No. 2,658,072, N-higher alkyl aspartic acids such as those produced according to the teaching of U.S. Pat. No. 2,438,091, and the products sold under the trade name "MIRANOL"™ and described in U.S. Pat. No. 2,528,378.

Other amphoterics, sometimes classified as zwitterionics, such as betaines can also be used in the present invention. Such zwitterionics are considered as amphoterics in the present invention where the zwitterionic has an attached group that is anionic at the pH of the composition. Examples of betaines useful herein include the high alkyl betaines, such as coco dimethyl carboxymethyl betaine, cocoamidopropyl betaine, cocobetaine, lauryl amidopropyl betaine, oleyl betaine, lauryl dimethyl carboxymethyl betaine, lauryl dimethyl alphacarboxyethyl betaine, cetyl dimethyl carboxymethyl betaine, lauryl bis-(2-hydroxyethyl) carboxymethyl betaine, stearyl bis-(2-hydroxypropyl) carboxymethyl betaine, oleyl dimethyl gamma-carboxypropyl betaine, and lauryl bis-(2-hydroxypropyl)alpha-carboxyethyl betaine. The sulfobetaines may be represented by coco dimethyl sulfopropyl betaine, stearyl dimethyl sulfopropyl betaine, lauryl dimethyl sulfoethyl betaine, lauryl bis-(2-hydroxyethyl) sulfopropyl betaine and the like; amidobetaines and amidosulfobetaines, wherein the $RCONH(CH_2)_3$ radical is attached to the nitrogen atom of the betaine are also useful in this invention. Most preferred for use herein is cocoamidopropyl betaine.

Suitable anionic surfactants include alkyl sulfate, alkyl ethoxylated sulfate, or a mixture thereof. These materials have the respective formulae (I) $ROSO_3M$ and (II) $RO(C_2H_4O)_xSO_3M$, wherein R is alkyl or alkenyl of from about 8 to about 30 carbon atoms, x is 1 to 10, and M is H or a salt-forming cation such as ammonium, alkanolamine containing $C_1$–$C_3$ alkyl groups such as triethanolamine, and monovalent and polyvalent metals such as the alkaline and alkaline earth metals. Preferred metals include sodium, potassium, magnesium, and calcium. The cation M, of the anionic surfactant should preferably be chosen such that the anionic surfactant component is water soluble. Solubility of anionic surfactants, in general, will depend upon the particular anionic surfactants and cations chosen. As an aid to determining appropriate mixtures of anionic surfactants, the anionic surfactants should be chosen such that the Krafft temperature is about 15° C. or less, preferably about 10° C. or less, more preferably about 0° C. or less. It is also preferred that the anionic surfactant be soluble in the composition hereof.

Preferably, R has from about 10 to about 18 carbon atoms in both the alkyl and alkyl ethoxylated sulfates. The alkyl ethoxylated sulfates are typically made as condensation products of ethylene oxide and monohydric alcohols having from about 8 to about 24 carbon atoms. The alcohols can be derived from fats, e.g., coconut oil, palm kernel oil, or tallow, or can be synthetic. Such alcohols are preferably reacted with about I to about 10, more preferably from about 1 to about 4, most preferably from about 2 to about 3.5, molar proportions of ethylene oxide and the resulting mixture of molecular species having, for example, an average of 3 moles of ethylene oxide per mole of alcohol, is sulfated and neutralized.

Specific examples of alkyl ether sulfates which may be used in the present invention are sodium and ammonium salts of coconut alkyl triethylene glycol ether sulfate; tallow alkyl triethylene glycol ether sulfate, and tallow alkyl hexaoxyethylene sulfate. Highly preferred alkyl ether sulfates are those comprising a mixture of individual compounds, said mixture having an average alkyl chain length of from about 12 to about 16 carbon atoms and an average degree of ethoxylation of from about 1 to about 4 moles of ethylene oxide.

The sulfate surfactant is preferably comprised of a combination of ethoxylated and nonethoxylated sulfates. Alkyl sulfates can provide excellent cleaning and lather performance. Alkyl ethoxylated sulfates can provide excellent cleaning performance and are mild to the skin.

Other suitable anionic detersive surfactants include, but are not limited to water-soluble salts of organic, sulfuric acid reaction products of the general formula $[R_1\text{—}SO_3\text{—}M]$ where $R_1$ is selected from the group consisting of a straight or branched chain, saturated aliphatic hydrocarbon radical having from about 8 to about 24, preferably about 10 to about 18, carbon atoms; and M is a cation such as ammonium, alkanolamines, such as triethanolamine, monovalent metals, such as sodium and potassium, and polyvalent metal cations, such as magnesium, and calcium. The cation M, of the anionic detersive surfactant should be chosen such that the detersive surfactant component is water soluble. Solubility will depend upon the particular anionic detersive surfactants and cations chosen. Examples of such detersive surfactants are the salts of an organic sulfuric acid reaction product of a hydrocarbon of the methane series, including iso-, neo-, and n-paraffins, having about 8 to about 24 carbon atoms, preferably about 10 to about 18 carbon atoms and a sulfonating agent, e.g., $SO_3$, $H_2SO_4$, obtained according to known sulfonation methods, including bleaching and hydrolysis. Preferred are alkali metal and ammonium sulfonated $C_{10\text{-}18}$ n-paraffins.

Another class of anionic detersive surfactants suitable for use in the present invention are the reaction products of fatty acids esterified with isethionic acid and neutralized with sodium hydroxide where, for example, the fatty acids are derived from coconut oil or palm kernel oil; sodium, ammonium, tetraethylammonium or potassium salts of fatty acid amides of methyl tauride in which the fatty acids, for example, are derived from coconut oil or palm kernal oil. Other similar anionic surfactants are described in U.S. Pat. No. 2,486,921; U.S. Pat. No. 2,486,922; and U.S. Pat. No. 2,396,278, which descriptions are incorporated herein by reference.

Other anionic detersive surfactants suitable for use in the present invention are the succinnates, examples of which include disodium N-octadecylsulfosuccinnate; disodium lauryl sulfosuccinate; diammonium lauryl sulfosuccinate; tetrasodium N-(1,2-dicarboxyethyl)-N-octadecylsulfosuccinnate; diamyl ester of sodium sulfosuccinic acid; dihexyl ester of sodium sulfosuccinic acid; dioctyl esters of sodium sulfosuccinic acid.

Other suitable anionic detersive surfactants include alkyl glyceryl ether sulfonates and derivatives thereof.

Other suitable anionic detersive surfactants include olefin sulfonates having about 10 to about 24 carbon atoms. The term "olefin sulfonates" is used herein to mean compounds which can be produced by the sulfonation of alpha-olefins by means of uncomplexed sulfur trioxide, followed by neutralization of the acid reaction mixture in conditions such that any sulfones which have been formed in the reaction are hydrolyzed to give the corresponding hydroxy-alkanesulfonates. The sulfur trioxide can be liquid or gaseous, and is usually, but not necessarily, diluted by inert diluents, for example by liquid $SO_2$, chlorinated hydrocarbons, etc., when used in the liquid form, or by air, nitrogen, gaseous $SO_2$, etc., when used in the gaseous form.

The alpha-olefins from which the olefin sulfonates are derived are mono-olefins having about 10 to about 24 carbon atoms, preferably about 12 to about 16 carbon atoms. Preferably, they are straight chain olefins.

In addition to the true alkene sulfonates and a proportion of hydroxy-alkanesulfonates, the olefin sulfonates can contain minor amounts of other materials, such as alkene disulfonates depending upon the reaction conditions, proportion of reactants, the nature of the starting olefins and impurities in the olefin stock and side reactions during the sulfonation process.

A specific alpha-olefin sulfonate mixture of the above type is described more fully in the U.S. Pat. No. 3,332,880, which description is incorporated herein by reference.

Another class of anionic detersive surfactants suitable for use in the present invention are the beta-alkyloxy alkane sulfonates. These compounds have the following formula:

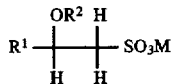

where $R^1$ is a straight chain alkyl group having from about 6 to about 20 carbon atoms, $R^2$ is a lower alkyl group preferably having from about 1 to about 3 carbon atoms, and M is a water-soluble cation as hereinbefore described.

Preferred additional anionic detersive surfactants for use in the present invention include alkyl glyceryl ether sulfonate, ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, sodium tridecyl benzene sulfonate, sodium dodecyl benzene sulfonate, and combinations thereof.

The anionic detersive surfactants are preferably present in the surfactant system of the present invention at a concentration level of from about 3% to about 20%, more preferably from about 4% to about 17%, most preferably from about 6% to about 14%.

Another class of anionic surfactants is fatty acid soaps. Though useful to the present invention, high concentrations of these surfactants in the presence of hard water tend to result in significant buildup on the hair and skin, adversely affecting cleansing and hair and skin feel. Accordingly, if added to the compositions of the present invention, the level of the fatty acid soaps is preferably incorporated at concentration levels of less than about 3%, more preferably less than about 1%.

The surfactant system of the present invention may also include nonionic surfactants, cationic surfactants, and combinations thereof. Suitable classes of nonionic surfactants include:

1. The polyethylene oxide condensates of alkyl phenols, e.g., the condensation products of alkyl phenols having an alkyl group containing from about 6 to about 12 carbon atoms in either a straight chain or branched chain configuration, with ethylene oxide, the said ethylene oxide being present in amounts equal to from about 10 to about 60 moles of ethylene oxide per mole of alkyl phenol. The alkyl substituent in such compounds may be derived from polymerized propylene, diisobutylene, octane, or nonane, for example.

2. Those derived from the condensation of ethylene oxide with the product resulting from the reaction of propylene oxide and ethylene diamine products which may be varied in composition depending upon the balance between the hydrophobic and hydrophilic elements which is desired. For example, compounds containing from about 40% to about 80% polyoxyethylene by weight and having a molecular weight of from about 5,000 to about 11,000 resulting from the reaction of ethylene oxide groups with a hydrophobic base constituted of the reaction product of ethylene diamine and excess propylene oxide, said base having a molecular weight of the order of about 2,500 to about 3,000, are satisfactory.

3. The condensation product of aliphatic alcohols having from about 8 to about 18 carbon atoms, in either straight chain or branched chain configuration, with ethylene oxide, e.g., a coconut alcohol ethylene oxide condensate having from about 10 to about 30 moles of ethylene oxide per mole of coconut alcohol, the coconut alcohol fraction having from about 10 to about 14 carbon atoms.

4. Long chain tertiary amine oxides corresponding to the following general formula:

wherein $R_1$ contains an alkyl, alkenyl or monohydroxy alkyl radical of from about 8 to about 18 carbon atoms, from 0 to about 10 ethylene oxide moieties, and from 0 to about 1 glyceryl moiety, and $R_2$ and $R_3$ contain from about 1 to about 3 carbon atoms and from 0 to about 1 hydroxy group, e.g., methyl, ethyl, propyl, hydroxyethyl, or hydroxypropyl radicals. The arrow in the formula is a conventional representation of a semipolar bond. Examples of amine oxides suitable for use in this invention include dimethyldodecylamine oxide, oleyldi(2-hydroxyethyl) amine oxide, dimethyloctylamine oxide, dimethyl-decylamine oxide, dimethyl-tetradecylamine oxide, 3,6,9-trioxaheptadecyldiethylamine oxide, di(2-hydroxyethyl)-tetradecylamine oxide, 2-dodecoxyethyldimethylamine oxide, 3-dodecoxy-2-hydroxypropyldi(3-hydroxypropyl) amine oxide, dimethylhexadecylamine oxide.

5. Long chain tertiary phosphine oxides corresponding to the following general formula:

wherein R contains an alkyl, alkenyl or monohydroxyalkyl radical ranging from about 8 to about 18 carbon atoms in chain length, from 0 to about 10 ethylene oxide moieties and from 0 to about 1 glyceryl moiety and R' and R" are each alkyl or monohydroxyalkyl groups containing from about 1 to about 3 carbon atoms. The arrow in the formula is a conventional representation of a semipolar bond. Examples of suitable phosphine oxides are: dodecyldimethylphosphine oxide, tetradecyldimethylphosphine oxide, tetradecylmethylethylphosphine oxide, 3,6,9,-trioxaoctadecyldimethylphosphine oxide, cetyldimethylphosphine oxide, 3-dodecoxy-2-hydroxypropyldi(2-hydroxyethyl) phosphine oxide, stearyldimethylphosphine oxide, cetylethylpropylphosphine oxide, oleyldiethylphosphine oxide, dodecyldiethylphosphine oxide, tetradecyldiethylphosphine oxide, dodecyldipropylphosphine oxide, dodecyldi(hydroxymethyl)phosphine oxide, dodecyldi(2-hydroxyethyl)phosphine oxide, tetradecylmethyl-2-hydroxypropylphosphine oxide, oleydimethylphosphine oxide, 2-hydroxydodecyldimethylphosphine oxide.

6. Long chain dialkyl sulfoxides containing one short chain alkyl or hydroxy alkyl radical of from about 1 to about 3 carbon atoms (usually methyl) and one long hydrophobic chain which include alkyl, alkenyl, hydroxy alkyl, or keto alkyl radicals containing from about 8 to about 20 carbon atoms, from 0 to about 10 ethylene oxide moieties and from 0 to about 1 glyceryl moiety. Examples include:

octadecyl methyl sulfoxide, 2-ketotridecyl methyl sulfoxide, 3,6,9,-trixaoctadecyl 2-hydroxyethyl sulfoxide, dodecyl methyl sulfoxide, oleyl 3-hydroxypropyl sulfoxide, tetradecyl methyl sulfoxide, 3-methoxytridecyl methyl sulfoxide, 3-hydroxytridecyl methyl sulfoxide, 3-hydroxy-4-dodecoxybutyl methyl sulfoxide.

7. Polyalkylene oxide modified dimethylpolysiloxanes, also known as dimethicone copolyols. These materials include the polyalkylene oxide modified dimethylpolysiloxanes of the following formulae:

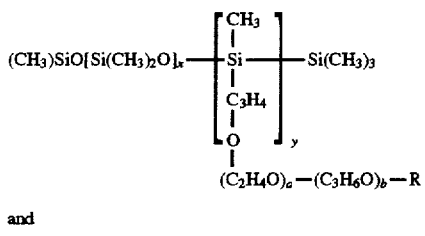

and

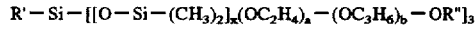

wherein R is hydrogen, an alkyl group having from 1 to about 12 carbon atoms, an alkoxy group having from 1 to about 6 carbon atoms or a hydroxyl group; R' and R" are alkyl groups having from 1 to about 12 carbon atoms; x is an integer of from 1 to 100, preferably from 20 to 30; y is an integer of 1 to 20, preferably from 2 to 10; and a and b are integers of from 0 to 50, preferably from 20 to 30. Dimethicone copolyols among those useful herein are disclosed in the following patent documents, all incorporated by reference herein: U.S. Pat. No. 4,122,029, Gee et al., issued Oct. 24, 1978; U.S. Pat. No. 4,265,878, Keil, issued May 5, 1981; and U.S. Pat. No. 4,421,769, Dixon et al., issued Dec. 20, 1983. Commercially available dimethicone copolyols, useful herein, include Silwet Surface Active Copolymers (manufactured by the Union Carbide Corporation); Dow Corning Silicone Surfactants (manufactured by the Dow Corning Corporation); Silicone Copolymer F-754 (manufactured by SWS Silicones Corp.); and Rhodorsil 70646 Fluid (manufactured by Rhone Poulenc, Inc.).

Cationic surfactants are also useful in compositions of the present invention and typically contain amino or quaternary ammonium hydrophilic moieties which are positively charged when dissolved in the aqueous composition of the present invention. Cationic surfactants among those useful herein are disclosed in the following documents, all incorporated by reference herein: M. C. Publishing Co., *McCutcheon's, Detergents & Emulsifiers*, (North American edition 1989); Schwartz, et al., *Surface Active Agents. Their Chemistry and Technology*, New York: Interscience Publishers, 1949; U.S. Pat. No. 3,155,591, Hilfer, issued Nov. 3, 1964; U.S. Pat. No. 3,929,678, Laughlin et al., issued Dec. 30, 1975; U.S. Pat. No. 3,959,461, Bailey et al., issued May 25, 1976; and U.S. Pat. No. 4,387,090, Bolich, Jr., issued Jun. 7, 1983. If included in the compositions of the present invention, the cationic surfactant must not interfere with the in-use performance and end-benefits of the personal care composition.

Among the quaternary ammonium-containing cationic surfactant materials useful herein are those of the general formula:

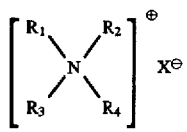

wherein $R_1$–$R_4$ are independently an aliphatic group of from about 1 to about 22 carbon atoms, or an aromatic, alkoxy, polyoxyalkylene, alkylamido, hydroxyalkyl, aryl or alkylaryl group having from about 12 to about 22 carbon atoms; and X is an anion selected from halogen, acetate, phosphate, nitrate and alkylsulfate radicals. The aliphatic groups may contain, in addition to carbon and hydrogen atoms, ether linkages, and other groups such as amino groups.

Other quaternary ammonium salts useful herein have the formula:

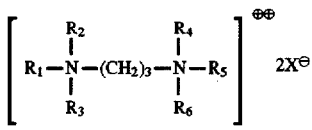

wherein $R_1$ is an aliphatic group having from about 16 to about 22 carbon atoms. $R_2$, $R_3$, $R_4$, $R_5$, and $R_6$ are selected from hydrogen and alkyl having from about 1 to about 4 carbon atoms, and X is an ion selected from halogen, acetate, phosphate, nitrate and alkyl sulfate radicals. Such quaternary ammonium salts include tallow propane diammonium dichloride.

Preferred quaternary ammonium salts include monoalkyltrimethylammonium chlorides and dialkyldimethylammonium chlorides and trialkyl methyl ammonium chlorides, wherein at least one of the alkyl groups have from about 12 to about 22 carbon atoms and are derived from long-chain fatty acids, such as hydrogenated tallow fatty acid (tallow fatty acids yield quaternary compounds wherein the long chain alkyl groups are predominately from 16 to 18 carbon atoms). Examples of quaternary ammonium salts useful in the present invention include stearyl trimethyl ammonium chloride, ditallowdimethyl ammonium chloride, ditallowdimethyl ammonium methyl sulfate, dihexadecyl dimethyl ammonium chloride, di(hydrogenated tallow) dimethyl ammonium chloride, dioctadecyl dimethyl ammonium chloride, dieicosyl dimethyl ammonium chloride, didocosyl dimethyl ammonium chloride, di(hydrogenated tallow) dimethyl ammonium acetate, dihexadecyl dimethyl ammonium chloride, dihexadecyl dimethyl ammonium acetate, ditallow dipropyl ammonium phosphate, ditallow dimethyl ammonium nitrate, di(coconutalkyl) dimethyl ammonium chloride, and stearyl dimethyl benzyl ammonium chloride, ditallow dimethyl ammonium chloride, dicetyl dimethyl ammonium chloride, stearyl dimethyl benzyl ammonium chloride and cetyl trimethyl ammonium chloride are preferred quaternary ammonium salts useful herein. Di(hydrogenated tallow) dimethyl ammonium chloride and tricetyl methyl ammonium chloride are particularly preferred quaternary ammonium salts. These materials also provide anti-static benefits to shampoo embodiments of the present invention.

Other surfactants known in the art for use in hair or personal cleansing products may be used in the surfactant system of the present invention, provided that the surfactant is also chemically and physically compatible with the essential components of the present invention, or does not otherwise unduly impair product performance, aesthetics or stability. Preferred for use in the surfactant system of the present invention are anionic and/or amphoteric surfactants.

Though useful to the compositions of the present invention, nonionic or cationic surfactants tend to reduce the lathering properties of soap and shampoo compositions. To maintain adequate lathering profiles, nonionic or cationic surfactants are preferably present at low concentrations. Generally, the surfactant system of the present invention will contain less than 3%, more preferably less than 1% of the nonionic and cationic surfactant.

Nonionic or Anionic Water-Soluble Polymer

Another essential component of the present invention is a nonionic or anionic water-soluble polymer. Suitable nonionic polymers include such water soluble polymers as cellulose ethers (e.g., hydroxybutyl methylcellulose, hydroxypropylcellulose, hydroxypropyl methylcellulose, ethylhydroxy ethylcellulose and hydroxyethylcellulose), propylene glycol alginates, polyacrylamide, poly(ethylene oxide), polyvinyl alcohol, polyvinylpyrrolidone, hydroxypropyl guar gum, locust bean gum, amylose, hydroxyethyl amylose, starch and starch derivatives and mixtures thereof. Preferred nonionic polymers include hydroxyethyl cellulose, polyethylene oxide, polyvinyl pyrrolidone, polyvinyl alcohol, polyacrylamide, hydroxypropyl cellulose, ethylhydroxyethyl cellulose, dextran, polypropyleneoxide and hydroxypropyl guar or mixtures thereof.

Suitable anionic water-soluble polymers include carboxymethyl cellulose, carrageenan, xanthum gum, polystyrene sulfonate, gum agar, gum ghatti, gum karaya, pectins, alginate salts, as well as poly(acrylic acid) and acrylic or methacrylic acid derivatives such as the alkali metal and ammonium salts of acrylic acid, methacrylic acid. Mixtures of the above anionic water-soluble polymers may also be used.

These polymeric compositions may be homopolymers or they may be copolymers or terpolymers with other copolymerizing monomers known in the art. Examples of copolymerizing monomers known in the art include but are not limited to ethylene, propylene, isobutylene, styrene, polystyrene, alphamethylstyrene, vinyl acetate, vinyl formate, alkyl ethers, acrylonitrile, methacrylonitrile, vinyl chloride, vinylidene chloride, the alkyl acrylates, the alkylmethacrylates, the alkyl fumarates, the alkyl maleates, and other olefinic monomers copolymerizable therewith as long as the resulting polymers are water soluble and phase separate in the compositions of this invention. Copolymers of anionic and nonionic monomers such as acrylic acid and methacrylic acid with acrylamide, methacrylamide, the N-alkyl substituted amides, the N-aminoalkylamides, the corresponding N-alkylaminoalkyl substituted amides, the aminoalkyl acrylates, the aminoalkyl methacrylamides, and the N-alkyl substituted aminoalkyl esters of either acrylic or methacrylic acids.

Preferred anionic polymers include polyacrylic acid; sodium carboxy methyl cellulose; polyacrylates; polymethyl acrylate; polysulphates such as polyvinyl sulfate, polystyrene sulfonate, polyphosphates, sodium dextran sulfate, alginate salts and pectate When combined with the aqueous surfactant system and phase separation initiator, described below, the water-soluble nonionic or anionic polymer separates to form aqueous droplets suspended in a continuous aqueous phase. The number average particle size of the polymer droplets can be from 0.1 microns to about 10,000 microns, preferably from about 1.0 micron to about 5000 microns, most preferably from about 5 microns to about 1000 microns.

Most preferred for use in the present invention are ethyl hydroxyethyl cellulose, hydroxyethyl cellulose, hydroxypropyl guar and polystyrene sulfonate.

The herein described polymers are preferably present at a concentration level of above about 0.1%, more preferably from about 0.15% to about 10%, most preferably from about 0.2% to about 2%, mixtures of the anionic and nonionic water-soluble polymers may also be used.

Phase Separation Initiators

Another essential component of the present invention is the phase separation initiator. By the term "phase separation initiators", as used herein, means electrolytes, amphiphiles or mixtures thereof capable of inducing phase separation when combined with compositions comprising a surfactant system and a nonionic or anionic water-soluble polymer.

By the term "amphiphile" as used herein, means, generally, substances which contain both hydrophilic and hydrophobic (lipophilic) groups. Amphiphiles preferred for use in the present invention are those which generally do not form micelles or liquid crystal phases and include, but are not limited to: amides of fatty acids; fatty alcohols; fatty esters, glycol mono- and di- esters of fatty acids; glyceryl esters.

Amides, including alkanol amides, are the condensation products of fatty acids with primary and secondary amines or alkanolamines to yield products of the general formula:

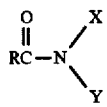

wherein RCO is a fatty acid radical and R is $C_{8-20}$; X is an alkyl, aromatic or alkanol (CHR'CH$_2$OH wherein R' is H or $C_{1-6}$ alkyl); Y is H, alkyl, alkanol or X. Suitable amides include, but are not limited to , cocamide, lauramide, oleamide and stearamide. Suitable alkanolamides include, but are not limited to, cocamide DEA, cocamide MEA, cocamide MIPA, isostearamide DEA, isostearamide MEA, isostearamide MIPA, lanolinamide DEA, lauramide DEA, lauramide MEA, lauramide MIPA, linoleamide DEA, linoleamide MEA, linoleamide MIPA, myristamide DEA, myristamide MEA, myristamide MIPA, Oleamide DEA, Oleamide MEA, Oleamide MIPA, palmamide DEA, palmamide MEA, palmamide MIPA, palmitamide DEA, palmitamide MEA, palm kernelamide DEA, palm kernelamide MEA, palm kernelamide MIPA, peanutamide MEA, peanutamide MIPA, soyamide DEA, stearamide DEA, stearamide MEA, stearamide MIPA, tallamide DEA, tallowamide DEA, tallowamide MEA, undecylenamide DEA, undecylenamide MEA. The condensation reaction may be carried out with free fatty acids or with all types of esters of the fatty acids, such as fats and oils, and particularly methyl esters. The reaction conditions and the raw material sources determine the blend of materials in the end product and the nature of any impurities.

Fatty alcohols are higher molecular weight, nonvolatile, primary alcohols having the general formula:

wherein R is a $C_{8-20}$ alkyl. They can be produced from natural fats and oils by reduction of the fatty acid COOH— grouping to the hydroxyl function. Alternatively, identical or similarly structured fatty alcohols can be produced according to conventional synthetic methods known in the art. Suitable fatty alcohols include, but are not limited to, behenyl alcohol, $C_{9-11}$ alcohols, $C_{12-13}$ alcohols, $C_{12-15}$ alcohols, $C_{12-16}$ alcohols, $C_{14-15}$ alcohols, caprylic alcohol, cetearyl alcohol, coconut alcohol, decyl alcohol, isocetyl alcohol, isostearyl alcohol, lauryl alcohol, oleyl alcohol, palm kernel alcohol, stearyl alcohol, cetyl alcohol, tallow alcohol, tridecyl alcohol or myristyl alcohol.

Glyceryl esters comprise a subgroup of esters which are primarily fatty acid mono- and di-glycerides or triglycerides modified by reaction with other alcohols and the like. Preferred glyceryl esters are mono and diglycerides. Suitable glyceryl esters and derivatives thereof include, but are not limited to, acetylated hydrogenated tallow glyceride, glyceryl behenate, glyceryl caprate, glyceryl caprylate, glyceryl caprylate/caprate, glyceryl dilaurate, glyceryl dioleate, glyceryl erucate, glyceryl hydroxystearate, glyceryl isostearate, glyceryl lanolate, glyceryl laurate, glyceryl linoleate, glyceryl oleate, glyceryl stearate, glyceryl myristate, glyceryl distearate and mixtures thereof.

Also useful as amphiphiles in the present invention are long chain glycol esters or mixtures thereof. Included are ethylene glycol esters of fatty acids having from about 8 to about 22 carbon atoms. Fatty esters of the formula RCO-OR' also act as suitable amphiphiles in the compositions of the present invention, where one of R and R' is a $C_{8-22}$ alkyl and the other is a $C_{1-3}$ alkyl.

The amphiphiles of the present invention may also encompass a variety of surface active compounds such as nonionic and cationic surfactants. If incorporated into the compositions of the present invention, these surface active compounds become additional surfactants used as amphiphiles for the purpose of initiating phase separation and are separate and apart from the surfactants of the surfactant system and the alkyl glyceryl sulfonate surfactant of the present invention.

Amphiphiles preferred for use herein include cocamide MEA, cetyl alcohol and stearyl alcohol.

The amphiphiles of the present invention are preferably present in the personal cleansing compositions at levels of from 0 to about 4%, preferably from about 0.5% to about 2%.

Suitable electrolytes include mono-, di- and trivalent inorganic salts as well as organic salts. Surfactant salts themselves are not included in the present electrolyte definition but other salts are. Suitable salts include, but are not limited to, phosphates, sulfates, nitrates, citrates and halides. The counter ions of such salts can be, but are not limited to, sodium, potassium, ammonium, magnesium or other mono-, di and tri valent cation. Electrolytes most preferred for use in the compositions of the present invention include sodium chloride, ammonium chloride, sodium citrate, and magnesium sulfate. It is recognized that these salts may serve as thickening aids or buffering aids in addition to their role as a phase separation initiator. The amount of the electrolyte used will generally depend on the amount of the amphiphile incorporated, but may be used at concentration levels of from about 0.1% to about 4%, preferably from about 0.2% to about 2%.

The amount of phase separation initiator comprising the electrolyte and/or the amphiphile will vary with the type of surfactant and polymer, but is generally present at a level of from about 0.1% to about 5%, preferably from about 0.2% to about 3%.

In view of the essential nature and activity of the phase separation initiators described above, the compositions of the present invention are, preferably, substantially free of materials which would prevent the induction or formation of separate, liquid phases. The term "substantially free", as used here, means that the compositions of the present invention contain no more than about 0.5% of such materials, preferably less than 0.25%, more preferably zero. Such materials typically include ethylene glycol, propylene glycol, ethyl alcohol and the like.

The compositions of the present invention are also preferably substantially free of other ingredients which unduly minimize the formation of separate and distinct liquid phases, especially ingredients which do not provide a significant benefit to the present invention.

Water

The personal cleansing compositions of the present invention comprise from about 50% to about 95%, preferably from about 60% to about 90%, more preferably from about 75% to about 85%, by weight of water.

Optional Ingredients

Silicone Components

The compositions of the present invention may optionally include non-volatile silicone conditioning components. Typically the silicone components are intermixed into aqueous personal cleansing compositions, forming a separate, discontinuous silicone phase. The silicone conditioning component will comprise a silicone fluid conditioning agent such as a silicone fluid and can also comprise other ingredients, such as a silicone resin to enhance silicone fluid deposition efficiency or enhance glossiness of the hair (especially when high refractive index (e.g. above about 1.46) silicone conditioning agents are used (e.g. highly phenylated silicones).

As used herein, "nonvolatile" refers to silicone material with little or no significant vapor pressure under ambient conditions, as is understood by those in the art. Boiling point under one atmosphere (atm) will preferably be at least about 250° C., more preferably at least about 275° C., most preferably at least about 300° C. Vapor pressure is preferably about 0.2mm Hg at 25° C. or less, preferably about 0.1 mm Hg at 25° C. or less.

The silicone conditioning agent phase may comprise volatile silicone, nonvolatile silicone, or mixtures thereof. Typically, if volatile silicones are present, it will be incidental to their use as a solvent or carrier for commercially available forms of nonvolatile silicone materials ingredients, such as silicone gums and resins.

The silicone conditioning agents for use in the compositions of the present invention preferably have a viscosity of from about 20 to about 2,000,000 centistokes, more preferably from about 1,000 to about 1,800,000 centistokes, even more preferably from about 10,000 to about 1,500,000 centistokes, most preferably from about 30,000 to about 1,000,000 centistokes, at 25° C. The viscosity can be measured by means of a glass capillary viscometer as set forth in Dow Corning Corporate Test Method CTM0004, Jul. 20, 1970.

Optional silicone fluid for use in the present compositions include silicone oils which are flowable silicone materials with a viscosity of less than 1,000,000 centistokes, preferably between about 5 and 1,000,000 centistokes, more preferably between about 10 and about 600,000 centistokes, more preferably between about 10 and about 500,000 centistokes, most preferably between 10 and 300,000 centistokes at 25° C. Suitable silicone oils include polyalkyl siloxanes, polyaryl siloxanes, polyalkylaryl siloxanes, polyether siloxane copolymers, and mixtures thereof Other insoluble, nonvolatile silicone fluids having conditioning properties can also be used.

Optional Silicone oils for use in the composition include polyalkyl or polyaryl siloxanes which conform to following formula:

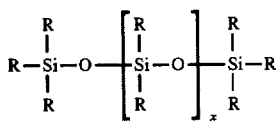

where R is aliphatic, preferably alkyl or alkenyl, or aryl, R can be substituted or unsubstituted, and x is an integer from 1 to about 8,000. Suitable unsubstituted R groups include alkoxy, aryloxy, alkaryl, arylalkyl, arylalkenyl, alkamino, and ether-substituted, hydroxyl-substituted, and halogen-substituted aliphatic and aryl groups. Suitable R groups also include cationic amines and quaternary ammonium groups.

The aliphatic or aryl groups substituted on the siloxane chain may have any structure as long as the resulting silicones remain fluid at room temperature, are hydrophobic, are neither irritating toxic nor otherwise harmful when applied to the hair or skin, are compatible with the other components of the herein described personal cleansing compositions, are chemically stable under normal use and storage conditions, are insoluble in the compositions of the present invention, and are capable of being deposited on and, of conditioning, the hair and skin.

The two R groups on the silicon atom of each monomeric silicone unit may represent the same group or different groups. Preferably, the two R groups represent the same group.

Preferred alkyl and alkenyl substituents are $C_1$-$C_5$ alkyls and alkenyls, more preferably from $C_1$-$C_4$, most preferably from $C_1$-$C_2$. The aliphatic portions of other alkyl-, alkenyl-, or alkynyl-containing groups (such as alkoxy, alkaryl, and alkamino) can be straight or branched chains and preferably have from one to five carbon atoms, more preferably from one to four carbon atoms, even more preferably from one to three carbon atoms, most preferably from one to two carbon atoms. As discussed above, the R substituents hereof can also contain amino functionalities, e.g. alkamino groups, which can be primary, secondary or tertiary amines or quaternary ammonium. These include mono-, di- and tri-alkylamino and alkoxyamino groups wherein the aliphatic portion chain length is preferably as described above. The R substituents can also be substituted with other groups, such as halogens (e.g. chloride, fluoride, and bromide), halogenated aliphatic or aryl groups, and hydroxy (e.g. hydroxy substituted aliphatic groups). Suitable halogenated R groups could include, for example, tri-halogenated (preferably fluoro) alkyl groups such as —$R^1$—$C(F)_3$, wherein $R^1$ is $C_1$-$C_3$ alkyl. Examples of such polysiloxanes include polymethyl-3,3,3 trifluoropropylsiloxane.

Suitable R groups include methyl, ethyl, propyl, phenyl, methylphenyl and phenylmethyl. The preferred silicones are polydimethyl siloxane, polydiethylsiloxane, and polymethylphenylsiloxane. Polydimethylsiloxane is especially preferred. Other suitable R groups include methyl, methoxy, ethoxy, propoxy, and aryloxy. The three R groups on the end caps of the silicone may also represent the same or different groups.

The nonvolatile polyalkylsiloxane fluids that may be used include, for example, polydimethylsiloxanes. These siloxanes are available, for example, from the General Electric Company in their Viscasil R and SF 96 series, and from Dow Corning in their Dow Coming 200 series.

The polyalkylaryl siloxane fluids that may be used, also include, for example, polymethylphenylsiloxanes. These siloxanes are available, for example, from the General Electric Company as SF 1075 methyl phenyl fluid or from Dow Corning as 556 Cosmetic Grade Fluid.

The polyether siloxane copolymers that may be used include, for example, a polypropylene oxide modified polydimethylsiloxane (e.g., Dow Corning DC-1248) although ethylene oxide or mixtures of ethylene oxide and propylene oxide may also be used. The ethylene oxide and polypropylene oxide level must be sufficiently low to prevent solubility in water and the composition hereof.

Other suitable silicone fluids for use in the silicone conditioning agents are insoluble silicone gums. These gums are polyorganosiloxane materials having a viscosity at 25° C. of greater than or equal to 1,000,000 centistokes. Silicone gums are described in U.S. Pat. No. 4,152,416; Noll and Walter, Chemistry and Technology of Silicones, New York: Academic Press 1968; and in General Electric Silicone Rubber Product Data Sheets SE 30, SE 33, SE 54 and SE 76, all of which are incorporated herein by reference. The silicone gums will typically have a mass molecular weight in excess of about 200,000, generally between about 200,000 and about 1,000,000, specific examples of which include polydimethylsiloxane, (polydimethylsiloxane) (methylvinylsiloxane) copolymer, poly(dimethylsiloxane) (diphenyl siloxane)(methylvinylsiloxane) copolymer and mixtures thereof.

The silicone conditioning agent can also comprise a mixture of polydimethylsiloxane gum (viscosity greater than about 1,000,000 centistokes) and polydimethylsiloxane oil (viscosity from about 10 to about 100,000 centistokes), wherein the ratio of gum to fluid is from about 30:70 to about 70:30, preferably from about 40:60 to about 60:40.

References disclosing examples of some suitable silicone fluids for use in the personal cleansing compositions include U.S. Pat. No. 2,826,551, U.S. Pat. No. 3,964,500, U.S. Pat. No. 4,364,837, British Patent 849,433, and Silicon Compounds, Petrarch Systems, Inc. (1984), all of which are incorporated herein by reference.

Silicone resins can be included in the silicone conditioning agent. These resins are highly crosslinked polymeric siloxane systems. The crosslinking is introduced through the incorporation of triftinctional and tetrafunctional silanes with monofunctional or difunctional, or both, silanes during manufacture of the silicone resin. As is well understood in the art, the degree of crosslinking that is required in order to result in a silicone resin will vary according to the specific silane units incorporated into the silicone resin. In general, silicone materials which have a sufficient level of trifunctional and tetrafunctional siloxane monomer units (and hence, a sufficient level of crosslinking) such that they dry down to a rigid, or hard, film are considered to be silicone resins. The ratio of oxygen atoms to silicon atoms is indicative of the level of crosslinking in a particular silicone material. Silicone materials which have at least about 1.1 oxygen atoms per silicon atom will generally be silicone resins herein. Preferably, the ratio of oxygen:silicon atoms is at least about 1.2:1.0. Silanes used in the manufacture of silicone resins include monomethyl-, dimethyl-, trimethyl-, monophenyl-, diphenyl-, methylphenyl-, monovinyl-, and methylvinyl-chlorosilanes, and tetrachlorosilane, with the methyl-substituted silanes being most commonly utilized. Preferred resins are offered by General Electric as GE SS4230 and SS4267. Commercially available silicone resins will generally be supplied in a dissolved form in a low viscosity volatile or nonvolatile silicone fluid. The silicone resins for use herein should be supplied and incorporated into the present compositions in such dissolved form, as will be readily apparent to those skilled in the art.

Background material on silicones including sections discussing silicone fluids, gums, and resins, as well as manufacture of silicones, can be found in Encyclopedia of Polymer Science and Engineering, Volume 15, Second Edition, pp. 204–308, John Wiley & Sons, Inc., 1989, incorporated herein by reference.

Silicone materials and silicone resins in particular, can conveniently be identified according to a shorthand nomenclature system well known to those skilled in the art as "MDTQ" nomenclature. Under this system, the silicone is described according to presence of various siloxane monomer units which make up the silicone. Briefly, the symbol M denotes the monofunctional unit $(CH_3)_3SiO_5$; D denotes the difunctional unit $(CH_3)_2SiO$; T denotes the trifunctional unit $(CH_3)SiO_{1.5}$; and Q denotes the quadri- or tetra-functional unit $SiO_2$. Primes of the unit symbols, e.g., M', D', T', and Q' denote substituents other than methyl, and must be specifically defined for each occurrence. Typical alternate substituents include groups such as vinyl, phenyls, amines, hydroxyls, etc. The molar ratios of the various units, either in terms of subscripts to the symbols indicating the total number of each type of unit in the silicone (or an average thereof) or as specifically indicated ratios in combination with molecular weight complete the description of the silicone material under the MDTQ system. Higher relative molar amounts of T, Q, T' and/or Q' to D, D', M and/or M' in a silicone resin is indicative of higher levels of crosslinking. As discussed before, however, the overall level of crosslinking can also be indicated by the oxygen to silicon ratio.

The silicone resins for use herein which are preferred are MQ, MT, MTQ, MDT and MDTQ resins. Thus, the preferred silicone substituent is methyl. Especially preferred are MQ resins wherein the M:Q ratio is from about 0.5:1.0 to about 1.5:1.0 and the average molecular weight of the resin is from about 1000 to about 10,000.

The weight ratio of the nonvolatile silicone fluid, having refractive index below 1.46, to the silicone resin component, when used, is preferably from about 4:1 to about 400:1, preferably this ratio is from about 9:1 to about 200:1, more preferably from about 19:1 to about 100:1, particularly when the silicone fluid component is a polydimethylsiloxane fluid or a mixture of polydimethylsiloxane fluid and polydimethylsiloxane gum as described above. Insofar as the silicone resin forms a part of the same phase in the compositions hereof as the silicone fluid, i.e. the conditioning active, the sum of the fluid and resin should be included in determining the level of silicone conditioning agent in the composition.

The number average particle size of the optional silicone component can vary widely depending on the formulation and/or the desired characteristics. Number average particle sizes preferred for use in the present invention range from about 10 nanometers to about 100 microns, more preferably from about 30 nanometers to about 20 microns.

Other Optional Components

The personal cleansing compositions of the present invention may further comprise one or more optional components known for use in shampoo, conditioning and other personal cleansing compositions, provided that the optional components are physically and chemically compatible with the essential component described herein, or do not otherwise unduly impair product stability, aesthetics or performance. Concentrations of such optional components typically range from about 0.001% to about 30% by weight of the personal cleansing compositions.

Optional components include anti static agents, cationic conditioning polymers such as polyquaternium-10, dyes, organic solvents or diluents, emollient oils (such as polyisobutylene, mineral oil, petrolatum and isocetyl stearyl stearate), pearlescent aids, foam boosters, pediculocides, pH adjusting agents, perfumes, preservatives, proteins, antioxidants; chelators and sequestrants; and aesthetic components such as fragrances, colorings, essential oils, skin sensates, astringents, skin soothing agents, skin healing agents and the like, nonlimiting examples of these aesthetic components include panthenol and derivatives (e.g. ethyl panthenol), pantothenic acid and its derivatives, clove oil, menthol, camphor, eucalyptus oil, eugenol, menthyl lactate, witch hazel distillate, allantoin, bisabalol, dipotassium glycyrrhizinate and the like, suspending agents, styling polymers, sunscreens, thickeners, vitamins and derivatives thereof (e.g., ascorbic acid, vitamin E, tocopheryl acetate, retinoic acid, retinol, retinoids, and the like), and viscosity adjusting agents. This list of optional components is not meant to be exclusive, and other optional components can be used.

Method of Manufacture

The compositions of the present invention, in general, can be made by mixing together at elevated temperature, e.g., about 72° C. water and surfactants along with any solids (e.g., amphiphiles) that need to be melted, to speed mixing into the personal cleansing composition. Additional ingredients including the electrolytes can be added either to this hot premix or after cooling the premix. The nonionic or anionic polymers can be added as a water solution after cooling the premix. The ingredients are mixed thoroughly at the elevated temperature and then pumped through a high shear mill and then through a heat exchanger to cool them to ambient temperature. The silicone may be emulsified at room temperature in concentrated surfactant and then added to the cooled product.

Alternately, for example, the silicone conditioning agent can be mixed with anionic surfactant and fatty alcohol, such as cetyl and stearyl alcohols, at elevated temperature, to form a premix containing dispersed silicone. The premix can then be added to and mixed with the remaining materials of the personal cleansing composition, pumped through a high shear mill, and cooled.

Method of Use

The personal cleansing compositions of the present invention are used in a conventional manner for cleansing and conditioning hair or skin. An effective amount of the composition for cleansing and conditioning the hair or skin is applied to the hair or skin, that has preferably been wetted with water, and then rinsed off. Such effective amounts generally range from about 1 g to 10 about 50 g, preferably from about 1 g to about 20 g. Application to the hair typically includes working the composition through the hair such that most or all of the hair is contacted with the composition.

This method for cleansing and conditioning the hair and skin comprises the steps of:

a) wetting the hair and/or skin with water, b) applying an effective amount of the personal cleansing composition to the hair and/or skin, and c) rinsing the composition from the hair and/or skin using water. These steps can be repeated as many times as desired to achieve the desired cleansing and conditioning benefit.

EXAMPLES

The personal cleansing compositions illustrated in Examples I–VIII illustrate specific embodiments of the personal cleansing compositions of the present invention, but are not intended to be limiting thereof. Other modifications can be undertaken by the skilled artisan without departing from the spirit and scope of this invention. These exemplified embodiments of the personal cleansing compositions of the present invention provide cleansing of hair and/or skin and improved conditioning.

All exemplified compositions can be prepared by conventional formulation and mixing techniques. Component amounts are listed as weight percents and exclude minor materials such as diluents, filler, and so forth. The listed formulations, therefore, comprise the listed components and any minor materials associated with such components.

| Ingredients | I | II | III | IV | V |
|---|---|---|---|---|---|
| Ammonium Laureth Sulfate | 5.00 | — | — | — | — |
| Ammonium Lauryl Sulfate | 5.00 | 7.50 | 7.50 | 7.50 | 7.50 |
| Sodium alkyl glycerol sulfonate | 2.50 | 2.50 | 2.50 | 2.50 | 2.50 |
| Cocoamidopropyl Betaine | — | — | — | — | — |
| Glycol Distearate | 2.00 | 1.50 | 2.00 | 2.00 | 2.00 |
| Cocomonoethanol amide | 0.60 | 0.85 | 0.85 | 0.85 | 0.85 |
| Cetyl Alcohol | 0.42 | 0.42 | 0.42 | 0.42 | 0.42 |
| Stearyl Alcohol | 0.18 | 0.18 | 0.18 | 0.18 | 0.18 |
| EDTA (ethylenediamine tetra acetic acid) | 0.10 | 0.10 | 0.10 | 0.10 | 0.10 |
| Monosodium phosphate | 0.10 | 0.10 | 0.10 | 0.10 | 0.10 |
| Disodium phosphate | 0.20 | 0.20 | 0.20 | 0.20 | 0.20 |
| Sodium Benzoate | 0.25 | 0.25 | 0.25 | 0.25 | 0.25 |
| Hydroxyethylcellulose[1] | 0.10 | 0.25 | — | — | — |
| Hydroxypropyl Guar[2] | — | — | 0.25 | — | — |
| Hydroxyethylethylcellulose[3] | — | — | — | 0.25 | — |
| Polystyrene Sulfonate | — | — | — | — | 0.25 |
| Tricetyl methylammonium chloride | 0.58 | — | — | — | — |
| Perfume | 0.60 | 0.60 | 0.60 | 0.60 | 0.60 |
| Dimethicone | 1.00 | 1.50 | 1.50 | 1.50 | 1.50 |
| Glydant | 0.20 | 0.20 | 0.20 | 0.20 | 0.20 |
| NaCl | 0.20 | 0.30 | 0.30 | 1.00 | 0.30 |
| Water and minors | q.s. to 100% | | | | |

| Ingredients | VI | VII | VIII |
|---|---|---|---|
| Ammonium Laureth Sulfate | — | 9.00 | 8.00 |
| Ammonium Lauryl Sulfate | 6.00 | — | — |
| Sodium alkyl glycerol sulfonate | 1.00 | 2.50 | — |
| Cocoamidopropyl Betaine | — | 2.50 | — |
| Glycol Distearate | 1.50 | 1.50 | 2.00 |
| Cocomonoethanol amide | 0.85 | 0.85 | — |
| Cetyl Alcohol | 0.42 | 0.42 | 0.40 |
| Stearyl Alcohol | 0.18 | 0.18 | 0.18 |
| EDTA (ethylenediamine tetra acetic acid) | 0.10 | 0.10 | 0.10 |
| Monosodium phosphate | 0.10 | 0.10 | 0.10 |
| Disodium phosphate | 0.20 | 0.20 | 0.20 |
| Sodium Benzoate | 0.25 | 0.25 | 0.25 |
| Hydroxyethylcellulose[1] | 0.25 | 0.25 | 0.25 |
| Hydroxypropyl Guar[2] | — | — | — |
| Hydroxyethylethylcellulose[3] | — | — | — |
| Polystyrene Sulfonate | — | — | — |
| Tricetyl methylammonium chloride | — | — | — |
| Perfume | 0.60 | 0.60 | 0.60 |
| Dimethicone | 1.50 | 1.50 | — |
| Glydant | 0.20 | 0.20 | 0.20 |
| Sodium Lauroamphoacetate | — | — | 3.60 |
| Polyquaternium-10 | — | — | 0.20 |
| NaCl | 0.30 | 0.30 | — |
| Water and minors | q.s. to 100% | | |

[1]Natrosol 250 HHR from Aqualon
[2]Jaguar HP 60 from Rhone-Poulenc
[3]Bermocoll E411 FQ from Akzo Nobel

What is claimed is:

1. A personal cleansing composition in the form of a stable aqueous emulsion, comprising:
  a.) from about 4% to about 50%, by weight, of a surfactant system comprising at least one surfactant selected from the group consisting of an anionic, cationic, nonionic, amphoteric, and zwitterionic surfactants and mixtures thereof wherein said surfactant system comprises at least one surfactant selected from the group consisting of alkyl glyceryl sulfonate surfactants, derivatives thereof, and salts thereof,
  b.) from above about 0.1 % to less than 1.0%, by weight, of a water soluble polymer selected from the group consisting of nonionic polymers, anionic polymers and mixtures thereof;
  c.) from about 0.1% to about 5%, by weight, of a phase separation initiator selected from the group consisting of electrolytes, amphiphiles and mixtures thereof; and
  d.) from about 50% to about 95%, by weight, of water wherein said polymer forms visually distinct aqueous droplets in the aqueous surfactant system.

2. A personal cleansing composition according to claim 1, wherein the surfactant system is present at a concentration of from about 4% to about 30%, by weight.

3. A personal cleansing composition according to claim 1, wherein the surfactant system comprises from about 0.5% to about 20%, by weight, of the alkyl glyceryl sulfonate surfactant, derivatives thereof, or salts thereof.

4. A personal cleansing composition according to claim 1, wherein the nonionic or anionic polymer forms visually distinct aqueous droplets in the aqueous surfactant system.

5. A personal cleansing composition according to claim 4, wherein the number average particle size of the polymer droplets is greater than about 0.1 microns.

6. A personal cleansing composition according to claim 1, wherein the nonionic or anionic polymer is selected from the group consisting of hydroxyethyl cellulose, polyethylene oxide, polyvinyl pyrrolidone, polyvinyl alcohol, polyacrylamide, hydroxypropyl cellulose, ethylhydroxyethyl cellulose, dextran, polypropyleneoxide, hydroxypropyl guar, guar gums, polyacrylic acid polystyrene, sodium carboxy methyl cellulose, polycarboxylates, polysulphates, polyphosphates, sodium dextran sulfate, alginate, pectate, derivatives thereof and mixtures thereof.

7. A personal cleansing composition according to claim 6, wherein the nonionic and anionic polymer is selected from the group consisting of hydroxyethyl cellulose, ethylhydroxyethyl cellulose, hydroxypropyl guar, polystyrene and mixtures thereof.

8. A personal cleansing compositions according to claim 1, wherein the surfactant system further comprises an additional surfactant selected from the group consisting of ammonium lauryl sulfate, ammonium laureth sulphate, cocamidopropyl betaine, sodium lauroamphoacetate, derivatives thereof and mixtures thereof.

9. A personal cleansing composition according to claim 1, wherein the amphiphile is selected from the group consisting of cocamide MEA, cetyl alcohol, stearyl alcohol, derivatives thereof and mixtures thereof.

10. A personal cleansing composition according to claim 1, wherein the electrolyte is selected from the group of consisting of anions selected from the group consisting of phosphates, sulfates, nitrates, citrates, halides; cations selected from the group consisting of sodium, potassium, ammonium, magnesium; and mixtures thereof.

11. A personal cleansing composition according to claim 1, further comprising a silicone conditioning component.

12. A personal cleansing composition in the form of a stable aqueous emulsion, comprising:
  a.) from about 4% to about 50%, by weight, of a surfactant system comprising at least one surfactant selected from the group consisting of an anionic, cationic, nonionic, amphoteric, and zwitterionic surfactants and mixtures thereof wherein said surfactant system comprises at least one surfactant selected from the group consisting of alkyl glyceryl sulfonate surfactants, derivatives thereof, and salts thereof, b.) from above about 0.1% to less than 1.0%, by weight, of a water soluble polymer selected from the group consisting of nonionic polymers, anionic polymers and mixtures thereof;

c.) from about 0.1% to about 4%, by weight, of an electrolyte;

d.) from about 0% to about 4%, by weight, of an amphiphile; and e.) from about 50% to about 95%, by weight, of water wherein said polymer forms visually distinct aqueous droplets in the aqueous surfactant system.

13. A personal cleansing composition according to claim 12, wherein the nonionic and anionic polymer is selected from the group consisting of hydroxyethyl cellulose, ethylhydroxyethyl cellulose, hydroxypropyl guar, polystyrene mixtures thereof.

14. A personal cleansing compositions according to claim 12, wherein the surfactant system is selected from the group consisting of ammonium lauryl sulfate, ammonium laureth sulphate, cocamidopropyl betaine, sodium lauroamphoacetate, derivatives thereof and mixtures thereof.

15. A personal cleansing composition according to claim 12, wherein, the amphiphile is selected from the group consisting of cocamide MEA, cetyl alcohol, stearyl alcohol, derivatives thereof and mixtures thereof.

16. A personal cleansing composition according to claim 12, wherein the electrolyte is selected from the group of consisting of anions selected from the group consisting of phosphates, sulfates, nitrates, citrates, halides; cations selected from the group consisting of sodium, potassium, ammonium, magnesium; and mixtures thereof.

17. A composition according to claim 12, wherein the nonionic or anionic polymer forms visually distinct aqueous droplets in the aqueous surfactant system.

18. A method of treating hair by administering a safe and effective amount of the compositions according to claim 1.

19. A method of treating skin by administering a safe and effective amount of the compositions according to claim 1.

20. A method of cleaning hair and skin by administering a safe and effective amount of the compositions according to claim 1.

* * * * *